(12) United States Patent
Maier et al.

(10) Patent No.: US 11,648,362 B2
(45) Date of Patent: May 16, 2023

(54) FOLDABLE SUBTRATE AND PATIENT INTERFACE FORMED THEREFROM

(71) Applicant: KONINKLIJKE PHILIPS N.V., Eindhoven (NL)

(72) Inventors: James Robert Maier, Pittsburgh, PA (US); Lauren Patricia Chodkowski, Pittsburgh, PA (US); John Tompkins, Irwin, PA (US); Jonathan Sayer Grashow, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 746 days.

(21) Appl. No.: 16/585,011

(22) Filed: Sep. 27, 2019

(65) Prior Publication Data

US 2020/0101247 A1     Apr. 2, 2020

Related U.S. Application Data

(60) Provisional application No. 62/737,988, filed on Sep. 28, 2018.

(51) Int. Cl.
*A61M 16/06* (2006.01)
*B32B 7/12* (2006.01)

(52) U.S. Cl.
CPC ........... *A61M 16/0605* (2014.02); *B32B 7/12* (2013.01); *A61M 2016/0661* (2013.01); *A61M 2210/0618* (2013.01)

(58) Field of Classification Search
CPC ........... A61M 16/06–0694; A61M 2210/0618; A62B 7/10; A62B 18/02; A62B 18/025; A62B 23/02; A62B 23/025; A62B 23/06; B32B 7/12
See application file for complete search history.

(56) References Cited

U.S. PATENT DOCUMENTS

| 2,161,607 | A | * | 6/1939 | Anderson | A62B 23/06 128/206.18 |
|---|---|---|---|---|---|
| 4,354,489 | A | * | 10/1982 | Riaboy | A62B 23/06 55/DIG. 35 |
| 4,984,302 | A | * | 1/1991 | Lincoln | A41D 13/1176 2/206 |
| 5,740,798 | A | | 4/1998 | McKinney | |
| 6,098,624 | A | * | 8/2000 | Utamaru | A62B 23/06 128/206.14 |
| 7,121,279 | B2 | | 10/2006 | Dennis | |
| 8,276,588 | B1 | | 10/2012 | Connor | |
| 2006/0023228 | A1 | | 2/2006 | Zheng | |

(Continued)

FOREIGN PATENT DOCUMENTS

| CN | 105495775 | A | 4/2016 |
| CN | 106666872 | A | 5/2017 |

(Continued)

*Primary Examiner* — Valerie L Woodward
(74) *Attorney, Agent, or Firm* — Michael W. Haas (57) ABSTRACT

An apparatus including a patient interface device formed from a flat substrate that is folded, wherein the patient interface device includes a plurality of seams where sections of the substrate are joined together, and wherein one or more of the plurality of seams form a shape that corresponds to a perimeter of a bottom side of a nose from a first alare corner of the nose to a tip of the nose to a second alare corner of the nose.

14 Claims, 10 Drawing Sheets

(56) References Cited

U.S. PATENT DOCUMENTS

| | | | |
|---|---|---|---|
| 2009/0032019 A1* | 2/2009 | Green | A61M 15/0086 128/203.29 |
| 2009/0194107 A1* | 8/2009 | Loeser | A61M 15/08 128/206.13 |
| 2011/0253144 A1 | 10/2011 | Groll | |
| 2015/0027447 A1 | 1/2015 | Goldman et al. | |
| 2017/0072151 A1 | 3/2017 | Donnay | |
| 2017/0080173 A1 | 3/2017 | Paul et al. | |
| 2017/0326320 A1* | 11/2017 | Baigent | A61M 16/0683 |

FOREIGN PATENT DOCUMENTS

| | | | |
|---|---|---|---|
| WO | WO-03103775 A1 * | 12/2003 | A62B 23/06 |
| WO | 2015143595 A1 | 10/2015 | |
| WO | 2018124889 A1 | 7/2018 | |

\* cited by examiner

FOLDABLE SUBTRATE AND PATIENT INTERFACE FORMED THEREFROM

CROSS-REFERENCE TO RELATED APPLICATIONS

This patent application claims the priority benefit under 35 U.S.C. § 119(e) of U.S. Provisional Application No. 62/737,988, filed on Sep. 28, 2018, the contents of which are herein incorporated by reference.

BACKGROUND OF THE INVENTION

1. Field of the Invention

The present invention pertains to a pressure support systems, and, in particular, to patient interface devices for pressure support systems.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is a combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow followed by oxyhemoglobin desaturation and/or a cortical arousal. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a positive airway pressure (PAP) to the patient's airway using an airway pressure support system that typically includes a mask, a pressure generating device, and a conduit to deliver positive pressure breathing gas from the pressure generating device to the patient through the mask. This positive pressure effectively "splints" the airway, thereby maintaining an open passage to the lungs. In one type of PAP therapy, known as continuous positive airway pressure (CPAP), the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

Hospitals and sleep centers need extensive infrastructures and procedures to clean, track, and reuse patient interface devices safely. Patient interface devices are expensive and can cost patients tens to hundreds of dollars each. There is room for improvement in patient interface devices.

SUMMARY OF THE INVENTION

In accordance with an aspect of the disclosed concept, an apparatus comprises: a patient interface device formed from a flat substrate that is folded, wherein the patient interface device includes a plurality of seams where sections of the substrate are joined together, and wherein one or more of the plurality of seams form a shape that corresponds to a perimeter of a bottom side of a nose from a first alare corner of the nose to a tip of the nose to a second alare corner of the nose.

In accordance with an aspect of the disclosed concept, an apparatus comprises: a substrate being structured to be foldable to form a patient interface device, wherein the patient interface device includes a plurality of seams where sections of the substrate are joined together, and wherein one or more of the plurality of seams form a shape that corresponds to a perimeter of a nose from a first alare corner of the nose to a tip of the nose to a second alare corner of the nose.

In accordance with an aspect of the disclosed concept, an apparatus comprises: a first substrate being structured to be foldable to form a first part of a patient interface device, wherein the first part of the patient interface device is structured to cover a patient's nostrils and includes a plurality of seams where sections of the first substrate are joined together, and wherein one or more of the plurality of seams form a shape that corresponds to a perimeter of a bottom side of a nose from a first alare corner of the nose to a tip of the nose to a second alare corner of the nose; and a second substrate being structured to be foldable to form a second part of the patient interface device, wherein the second part of the patient interface device is structured to cover the patient's mouth, wherein the first part of the patient interface is structured to attach to the second part of the patient interface device to form the patient interface device.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
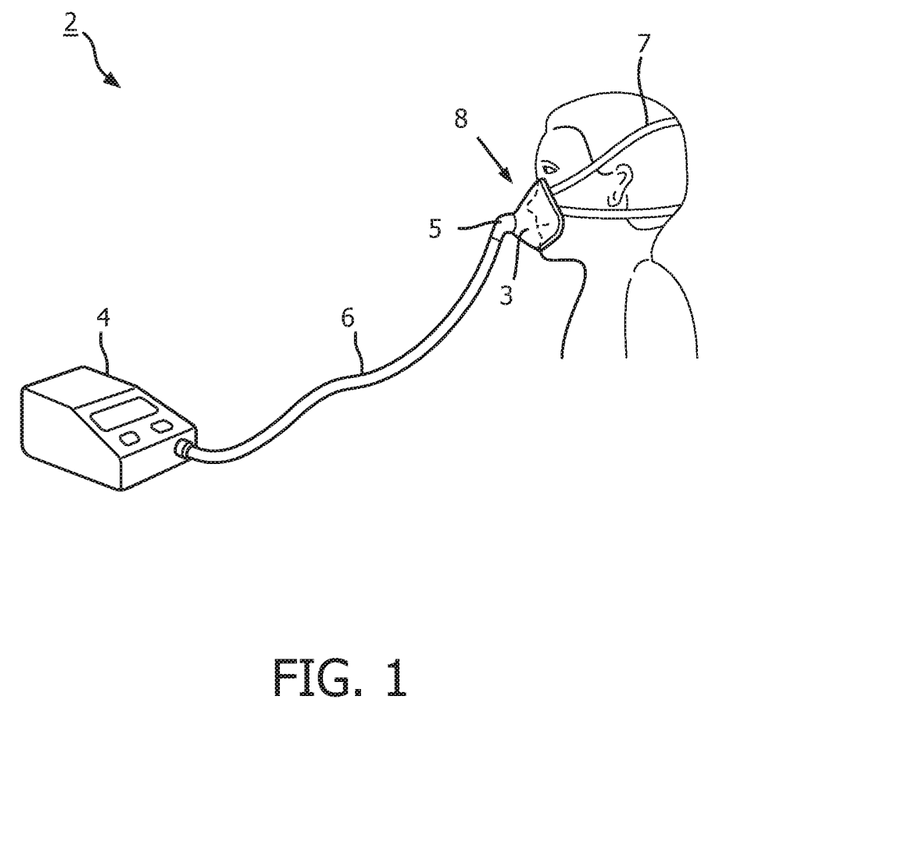
FIG. 1 is a diagram of a pressure support system according to an exemplary embodiment of the disclosed concept.

A system 2 adapted to provide a regimen of respiratory therapy to a patient is generally shown in FIG. 1. System 2 includes a pressure/flow generator 4, a delivery conduit circuit 6, a patient interface device 8 and a headgear 7 for securing patient interface device 8 to the head of a patient (not numbered). Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8. Delivery conduit 6 and patient interface device 8 are often collectively referred to as a patient circuit.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating device 4 is also referred to as a gas flow generating device, because flow results when a pressure gradient is generated. The present invention contemplates that pressure/flow generating device 4 is any conventional system for delivering a flow of gas to an airway of a patient or for elevating a pressure of gas at an airway of the patient, including the pressure support systems summarized above and non-invasive ventilation systems.

In the illustrated example system 2 of FIG. 1, patient interface device 8 is depicted as a nasal/oral mask which includes a patient sealing assembly in the form of a cushion 3 coupled to a generally rigid frame member of faceplate 5 which may be coupled to conduit 6 either directly or indirectly via any suitable coupling mechanism.

In accordance with example embodiments of the disclosed concept, new types of patient interface devices are provided that may be used in place of patient interface device 8 in system 2 of FIG. 1. Similarly, patient interface devices in accordance with embodiments of the disclosed concept may be employed in other pressure support therapy applications or other applications where a patient interface device or mask is employed.

Figure 2:
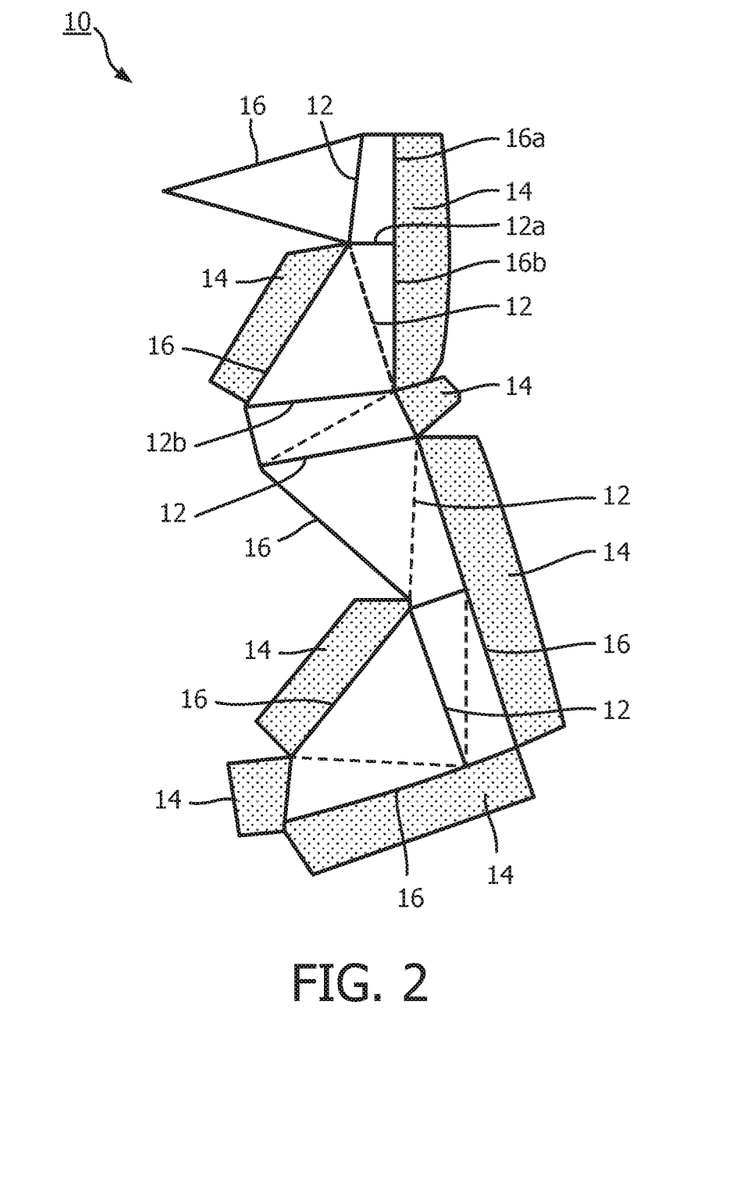
FIG. 2 is an illustration of a foldable substrate according to an exemplary embodiment of the disclosed concept.

FIG. 2 is an illustration of a substrate 10 that may be folded into a patient interface device in accordance with an example embodiment of the disclosed concept. FIGS. 3-7 are views of a patient interface device 20 formed by folding substrate 10 of FIG. 2.

Referring to FIG. 2, substrate 10 is substantially flat. Substrate 10 may be composed of a thin material such as, without limitation, paper, thin plastics, laminates, and/or fabrics or any combination of materials. However, it will be appreciated that many other types of materials may be employed in substrate 10. Any type of foldable material may be used as substrate 10. Substrate 10 is thin to a degree that it is easily foldable. For example, a thickness of substrate 10 is substantially less than a width or a length of substrate.

In an example embodiment, substrate 10 is a multilayered composite such as a laminate. For example, substrate 10 may have an intermediate adhesive layer. That is, top and bottom layers of substrate 10 may be non-adhesive. The top or bottom layers may be removed to expose the intermediate adhesive layer. In selected sections of substrate, top and or bottom layers may be selectively removed to expose the adhesive layer, thus creating adhesive sections 14 of substrate 10 where the adhesive layer is exposed. In some embodiments, a score line may be cut through the top and/or bottom layers allowing a user to subsequently peel off the top and/or bottom layers to expose the adhesive layer in adhesive sections 14 of substrate 10.

Substrate 10 is structured to be folded into patient interface device 20 shown in FIGS. 3-7. For example, substrate 10 has an outline perimeter shaped such that when substrate 10 is folded in a predetermined manner, substrate 10 will form patient interface device 20. Adhesive sections 14 may be used to adhere to other sections of substrate 10 to cause patient interface device 20 to hold its shape. Substrate 10 may be formed from a standard shaped sheet of material, such as a square or rectangular shaped sheet of material that is then cut to give substrate 10 its outline perimeter shape. The sheet of material may be cut using any suitable method. In some embodiments, it is contemplated that the sheet of material may be cut using a CNC cutter or other similar devices. In an example embodiment, the device used to cut substrate 10 is able to cut through some layers of substrate 10 without cutting through the entire substrate 10. Using this method, score lines may be cut into substrate allowing layers of substrate 10 to subsequently be peeled off in adhesive sections 14.

Substrate 10 includes fold lines 12 and seam lines 16. Fold lines 12 are where substrate 10 is folded in order to shape it into patient interface device 20. Seam lines 16 are where different sections of substrate 10 will join together and form seams in patient interface device 20. Seam lines 16 are formed by an outer perimeter of substrate 10 in areas where no adhesive sections 14 are located or along interior edges of adhesive sections 14. Sections of substrate 10 may be joined together to form seams using adhesive sections 14. However, it will be appreciated other attachment methods may also be employed without departing from the scope of the disclosed concept. For example and without limitation, sections of substrate 10 may be stitched together at seam lines 16 in order to join sections of substrate 10 together to create seams in patient interface device 20.

Figure 3:
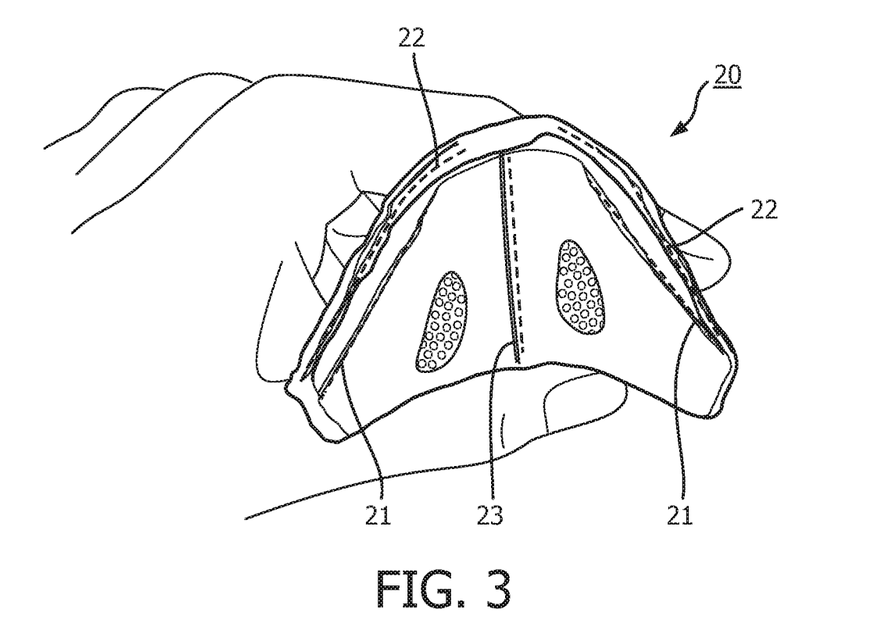
FIGS. 3-7 are illustrations of a patient interface device formed from the substrate of FIG. 2 in accordance with an exemplary embodiment of the disclosed concept.
Figure 4:
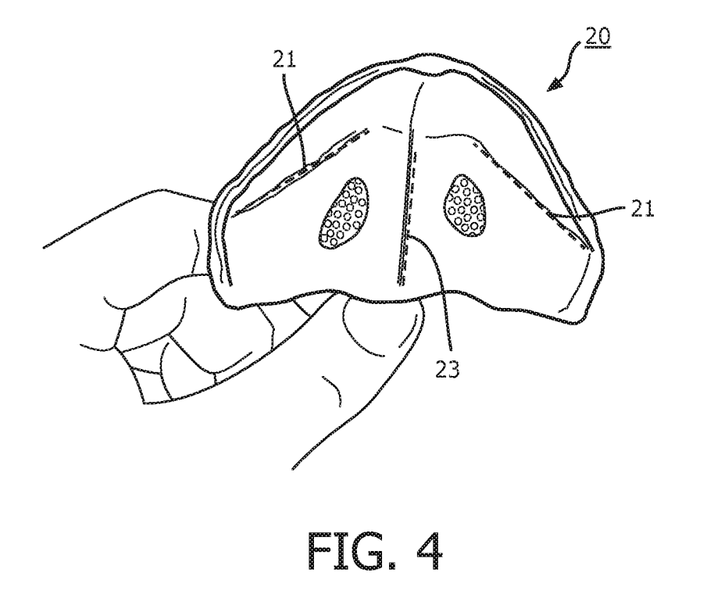

In an embodiment, seams are used to provide structure to patient interface device 20. Referring to FIGS. 3 and 4, patient interface device 20 may include a nasal interior perimeter seam 21 and a nasal exterior perimeter seam 22. Nasal interior and exterior perimeter seams 21, 22 have a shape that corresponds to a perimeter of a nose from one alare corner of the nose to the tip of the nose to the other alare corner of the nose. The nasal interior and exterior perimeter seams 21, 22 create stiff columns and add structure to patient interface device 20 that forces patient interface device 20 back into the alare corners of the nose to provide a stable seal. The nasal interior and exterior perimeter seams 21, 22 are created by joining sections of substrate 10 together at different seam lines 16. When patient interface device 20 is worn by a patient, nasal interior and exterior perimeter seams 21,22 will generally correspond in shape with the perimeter of the bottom of the patient's nose from the alare corners to the nose tip.

Patient interface device 20 also includes a centerline seam 23. Centerline seam 23 extends along a centerline of patient interface device 20. Centerline seam 23 provides additional structure for patient interface device 20. Centerline seam 23 may also be used to control a length of patient interface device 20. For example, centerline seam 23 may be formed from a seam line 16 of substrate 10 such as seam line 16b. Seam line 16b may be lengthened or shortened to adjust a length of patient interface device 20.

Figure 7:
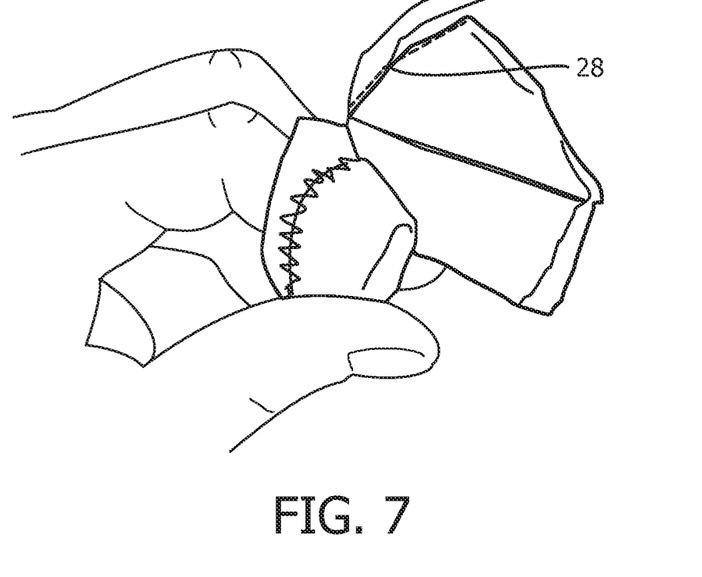

Referring to FIG. 7, patient interface device 20 also includes a height control seam 28. Height control seam 28 may be used to control a height of patient interface device 20. For example, height control seam 28 may be formed from a seam line 16 of substrate such as seam line 16b. Seam line 16b may be lengthened or shortened to adjust a length of patient interface device 20. Similarly, seam 27 may be adjusted to control other dimensions of patient interface device 20.

Various dimensions of patient interface device 20 may be controlled by controlling lengths of seam lines 16 of substrate 10. Similarly, various dimensions may be controlled by controlling lengths of fold lines 12 of substrate 10. For example, patient interface device 20 may include a nose tip width control fold 25 that may be formed for example by fold line 12a. Adjusting a length of fold line 12a can change the nose tip width of patient interface device 20. Similarly, patient interface device 20 may include a width control fold 26 that may be formed for example by fold line 12b. Adjusting a length of fold line 12b can change the width of patient interface device 20.

As described above, various seam lines 16 and fold lines 12 may be adjusted to change dimensions of patient interface device 20. It will be appreciated that substrate 10 and patient interface device 20 may be custom designed for a patient. For example, a scan of patient can be analyzed to determine key dimensions of a patient interface device that best fits the patient. Based on the key dimensions, various fold and seam lines 12, 16 of substrate 10 may be adjusted such that the resultant patient interface device 20 will have dimensions close or equal to the key dimensions determined from the scan of the patient.

In an embodiment, substrate 10 may include indicia. The indicia may be, for example, indications where substrate 10 should be folded in order to form patient interface device 20. When substrate 10 is folded along the indicia, substrate 10 will fold into the shape of patient interface device 20. The indicia may be, for example, lines printed on substrate 10 that correspond with the fold lines 12. However, it will be appreciated that other types of indicia may be used without departing from the scope of the disclosed concept.

Figure 5:
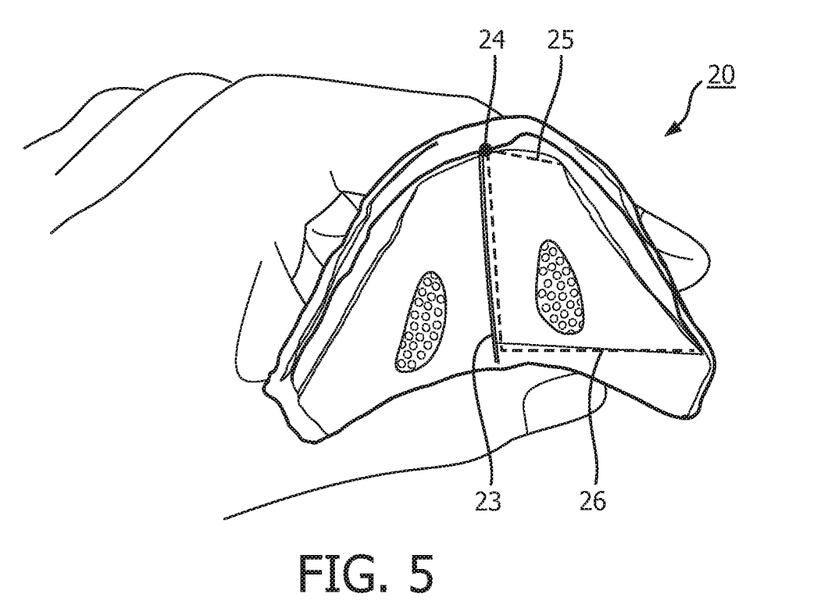
Figure 6:
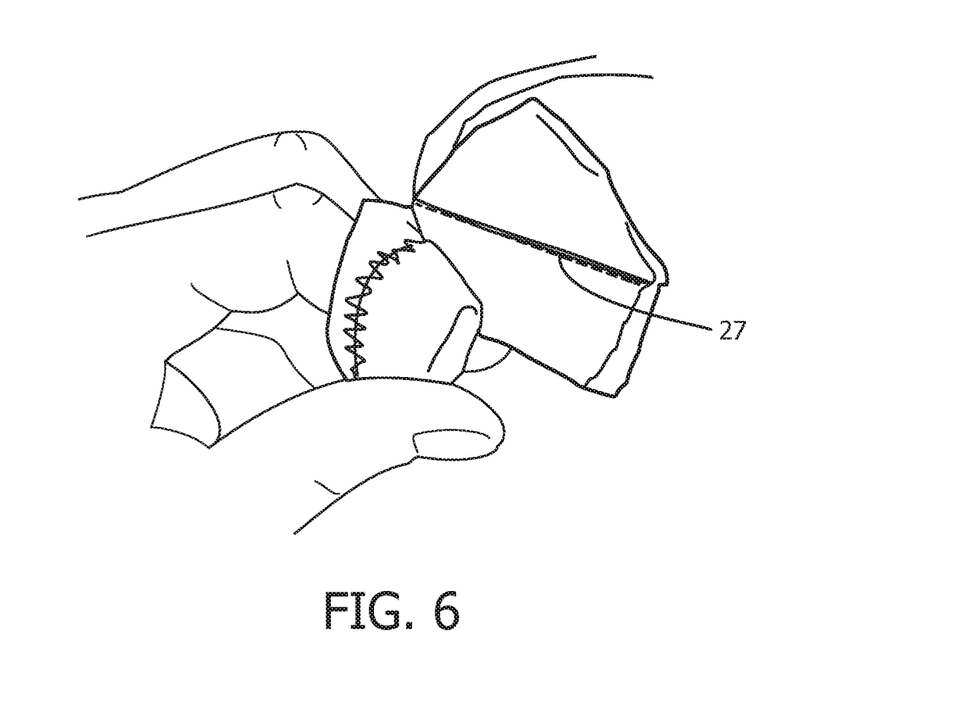

FIGS. 3-5 are front views of patient interface device 20 formed by folding substrate 10 and FIGS. 6 and 7 are side views of patient interface device 20 formed by folding substrate 10. Patient interface device 20 may include openings that correspond to openings of the nostrils of the patient. The openings may be formed in substrate 10 before it is folded into patient interface device 20 or they may be formed in patient interface device 20 after substrate 10 has been folded. FIGS. 2-7 provide an example of substrate 10 and patient interface device 20 that is formed from folding substrate 10. However, it will be appreciated that different types of substrates resulting in different types of patient interface devices may be employed without departing from the scope of the disclosed concept. Some examples will be described hereinafter.

Figure 8:
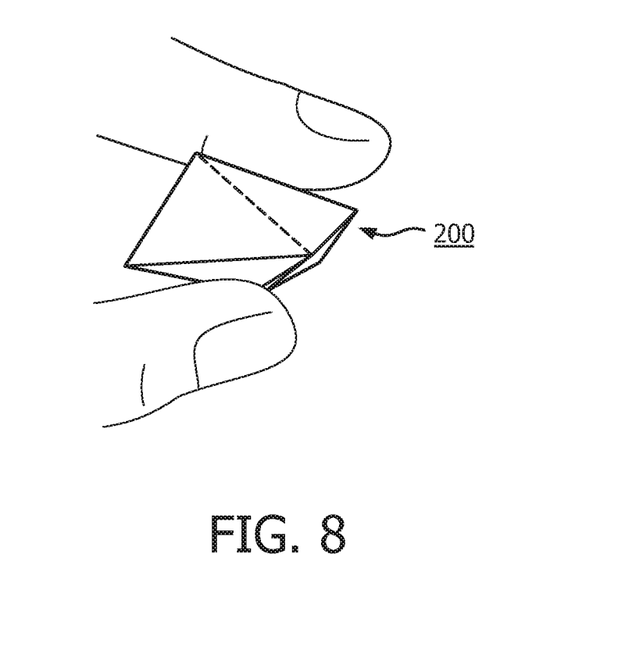
FIGS. 8-10 are illustrations of a patient interface device formed from a foldable substrate in accordance with an exemplary embodiment of the disclosed concept.
Figure 9:
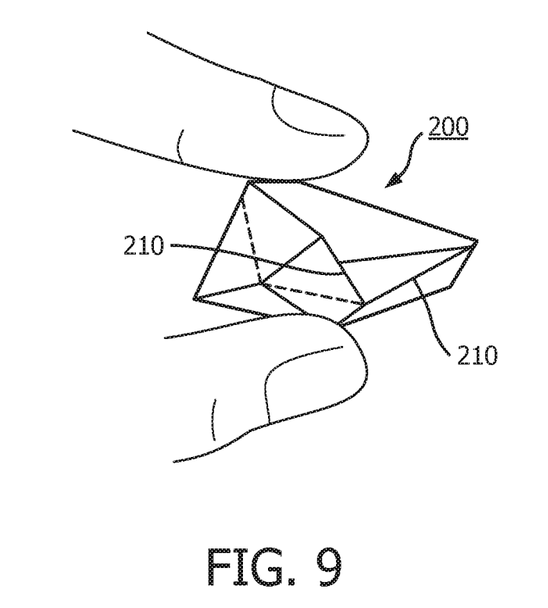
Figure 10:
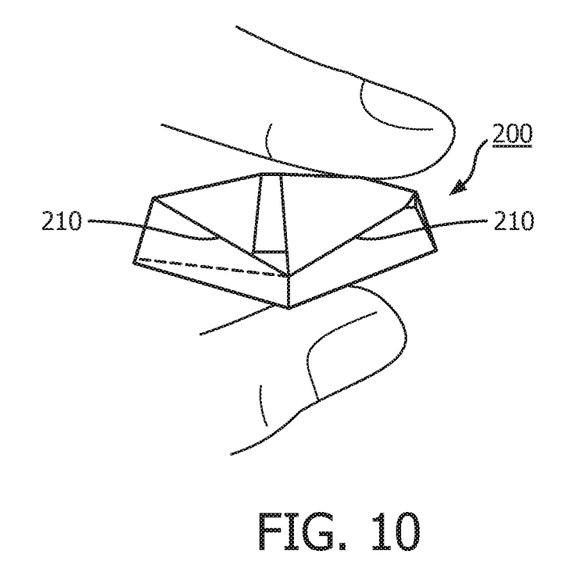

FIGS. 8-10 are views of a patient interface device 200 in accordance with an exemplary embodiment of the disclosed concept. Patient interface device 200 is formed by folding a substrate, similar to how patient interface device 20 is formed by folding substrate 10. FIG. 8 is a side view of patient interface device 200, FIG. 9 is an isometric view of patient interface device 200, and FIG. 10 is a front view of patient interface device 200. As shown in FIGS. 9 and 10, patient interface device 20 includes upper lip edges 210. Upper lip edges 210 are oriented such that they are placed along a patient's upper lip when patient interface device 200 is worn by the patient. Upper lip edges 210 are formed by sharp folds. The sharp folds force patient interface device 200 against the patient's nostrils when patient interface device 200 is worn by patient, thus creating a seal against patient and preventing leaks at corners of patient interface device 200.

As shown in FIG. 10, patient interface device 200 has a V-shape along its center line. The V-shape provides structural strength to patient interface device 200 and prevents it from collapsing.

Figure 11:
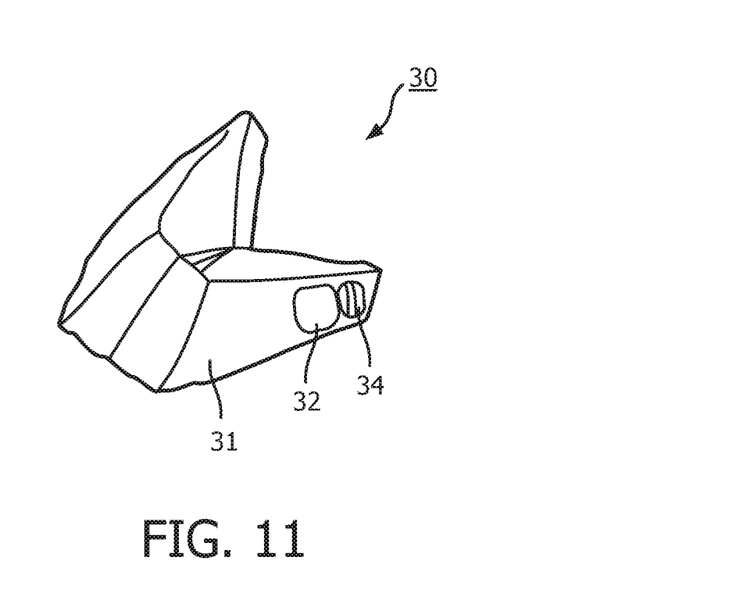
FIG. 11 is an illustration of a patient interface device formed from a foldable substrate and including a headgear tab in accordance with an exemplary embodiment of the disclosed concept.
Figure 12:
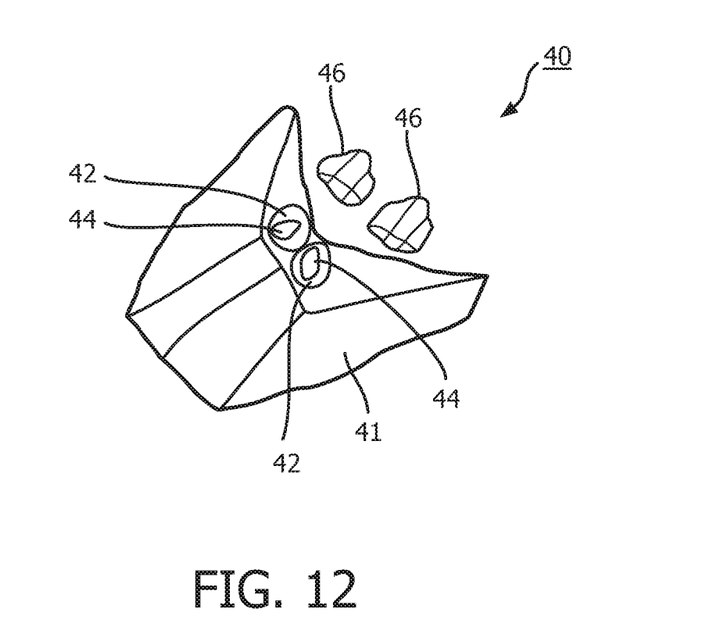
FIG. 12 is an illustration of a patient interface device formed from a foldable substrate and including nasal pillows according to an exemplary embodiment of the disclosed concept.

FIGS. 11 and 12 are illustrations of patient interface devices 30,40 including accessories according to exemplary embodiments of the disclosed concept. Referring to FIG. 11, patient interface device 30 includes a patient interface device body 31. Patient interface device body 31 is formed by folding a foldable substrate, similar to how patient interface device 20 is formed by folding substrate 10. Patient interface device body 31 includes an adhesive section 32. Patient interface device 30 also includes a headgear tab 34. Headgear tab 34 is used for connecting patient interface device 30 to headgear. Headgear tab 34 is secured to patient interface device body 31 by adhesive section 32.

Referring to FIG. 12, patient interface device 40 includes a patient interface device body 41. Patient interface device body 41 is formed by folding a foldable substrate, similar to how patient interface device 0 is formed by folding substrate 10. Patient interface device 40 includes openings 44 formed in patient interface device body 41 and adhesive sections 42 surrounding openings 44. Openings are formed in an area of patient interface device 40 such that when patient interface device 40 is worn by a patient, openings 44 will face the patient's nostrils. Openings 44 may have circular shapes and adhesive sections 42 may have circular shapes that surround openings 44. Patient interface device 40 also includes nasal pillows 46. Nasal pillows 46 may be any suitable type of nasal pillow employed in pressure support therapy applications or any other suitable type of nasal pillow. Nasal pillows 46 are structured to be placed on adhesive sections 42 and adhesive sections 42 are used to attach nasal pillows 46 to patient interface device body 41.

While FIGS. 11 and 12 illustrate two examples of how accessories can be employed with patient interface devices 30,40, it will be appreciated that other types of accessories may be employed without departing from the scope of the disclosed concept.

Figure 13:
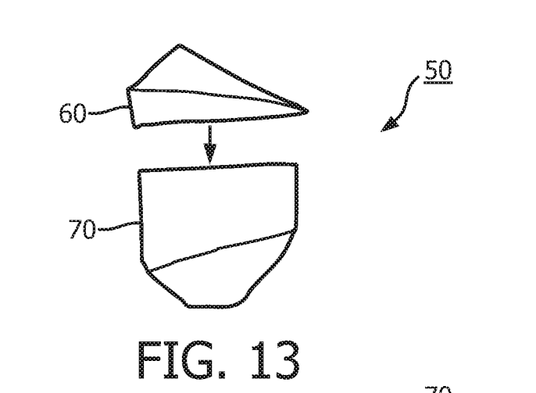
FIG. 13 is an illustration of a two-part patient interface device formed from two foldable substrates in accordance with an exemplary embodiment of the disclosed concept.

FIG. 13 is an illustration of a two-part patient interface device 50 according to an exemplary embodiment of the disclosed concept. Patient interface device 50 is formed from a top-part 60 and a bottom-part 70. Top-part 60 is formed by folding a first foldable substrate and bottom-part 70 is formed by folding a second foldable substrate. Top-part 60 and bottom-part 70 are attached to each other with adhesive sections including in the top-part 60, bottom-part 70, or both. Patient interface device 50 is a nasal/oral mask, meaning that it covers both a patient's nostrils and mouth.

Figure 14:
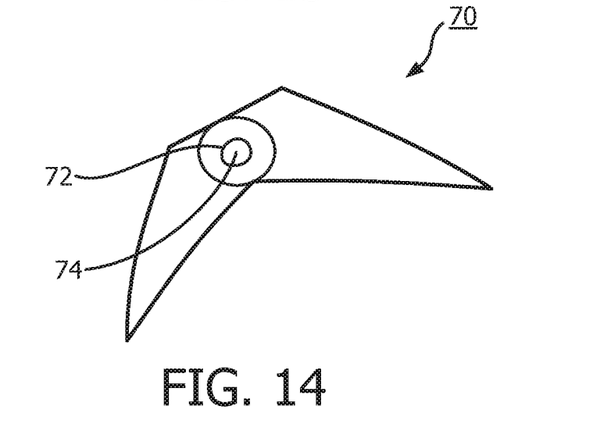
FIG. 14 is an illustration of the top part of the two-part patient interface device of FIG. 13.
Figure 15:
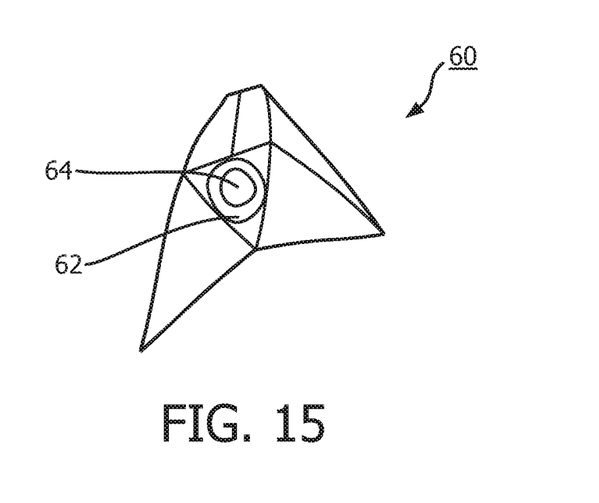
FIG. 15 is an illustration of the bottom part of the two-part patient interface device of FIG. 13.

FIG. 14 is an illustration of bottom-part 70 of patient interface device 80 of FIG. 13. FIG. 14 is a view taken from an upper surface of bottom-part 70. FIG. 15 is an illustration of top-part 60 of patient interface device 80. FIG. 10 is a view taken from a lower surface of top-part 60. Referring to FIG. 14, bottom-part 70 includes an adhesive section 72 and an opening 74. Referring to FIG. 15, top-part 60 also includes an adhesive section 62 and an opening 64. The adhesive sections 62,72 and openings 64,74 correspond to each other such that when top-part 60 and bottom-part 70 are joined together to form patient interface device 50, adhesive sections 62,72 attach top-part 60 and bottom-part 70 to each other and openings 64,74 are aligned such that air may flow through openings 64,74 from bottom-part 70 to top-part 60 and vice versa.

Figure 16:
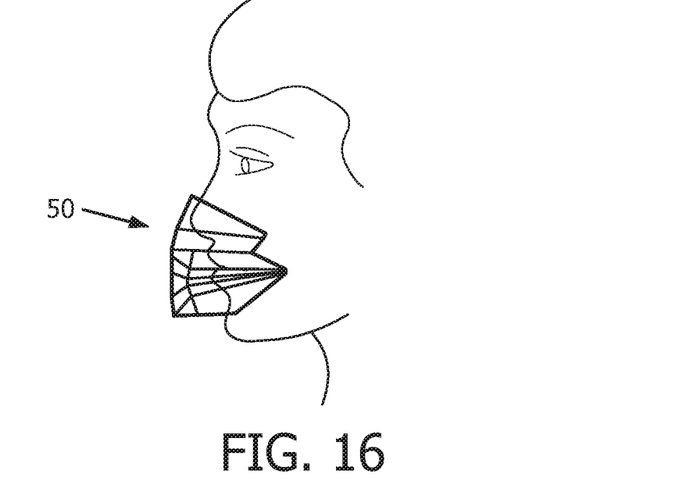
FIG. 16 is an illustration of the two-part patient interface device of FIG. 8 worn by a patient.

FIG. 16 is an illustration of patient interface device 50 being worn by a patient in accordance with an example embodiment of the disclosed concept. As shown in FIG. 16, patient interface device 50 is a nasal/oral mask that covers the patient's nose and mouth. While patient interface device 50 is described as having two parts in the present embodiment, it will be appreciated that in some embodiments a nasal/oral mask type patient interface may be formed by folding a single foldable substrate. Similarly, it will be appreciated that a nasal mask type patient interface device may be formed from multiple parts, each formed by foldable substrates, that are joined together. It will also be appreciated that the disclosed concept is not limited to one or two-part patient interface devices, but rather any number of patient interface devices formed from foldable substrates may be joined together without departing from the scope of the disclosed concept. It will also be appreciated that in some embodiments, full face mask type patient interfaces may be formed from one or more foldable substrates.

Figure 17:
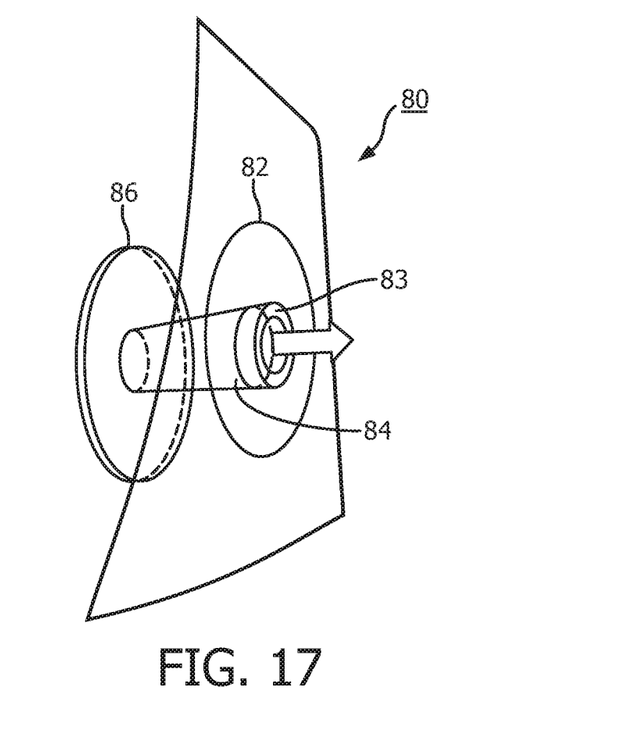
FIG. 17 is an illustration of an elbow connection being connected to a substrate according to an exemplary embodiment of the disclosed concept.

FIG. 17 is an illustration of an elbow 84 being joined to a substrate 80 according to an exemplary embodiment of the disclosed concept. Substrate 80 includes an opening 83 and an adhesive section 82. Elbow 84 is inserted into opening 83 until a flange 86 of elbow 84 contacts adhesive section 82. Flange 86 is adhered to adhesive section 82 such that elbow 84 becomes connected to substrate 80.

While FIG. 17 illustrates a substrate 80, it will be appreciated that substrate 80 may instead be a patient interface. For example, substrate 80 shown in FIG. 12 may be part of a foldable substrate that may be folded into a patient interface device such as how substrate 10 is folded into patient interface device 20. The subsequent patient interface device will include opening 83 and adhesive section 82 and elbow 84 may be inserted and flange 86 may adhere to adhesive section 82 as previously described. In this manner, elbow 84 may be attached to the patient interface device formed from substrate 80. It will be appreciated that elbow 84 may be attached to substrate 80 either before it is folded into a patient interface device or after it is folded into a patient interface device.

FIGS. 18-21 are views of a patient interface device 90 according to an exemplary embodiment of the disclosed concept. Patient interface device 90 is formed by folding a foldable substrate similar to how patient interface device 20 is formed from folding substrate 10. As noted above, different substrates which fold to form different patient interface devices are contemplated by the disclosed concept. Patient interface device 90 shown in FIGS. 13-16 is another example of a type of patient interface device that may be formed from a foldable substrate in accordance with disclosed concept.

Figure 18:
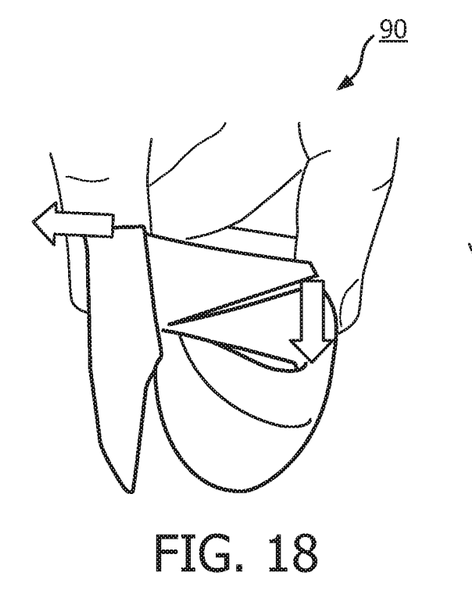
FIGS. 18-21 are views of a patient interface formed from a foldable substrate according to an exemplary embodiment of the disclosed concept.
Figure 19:
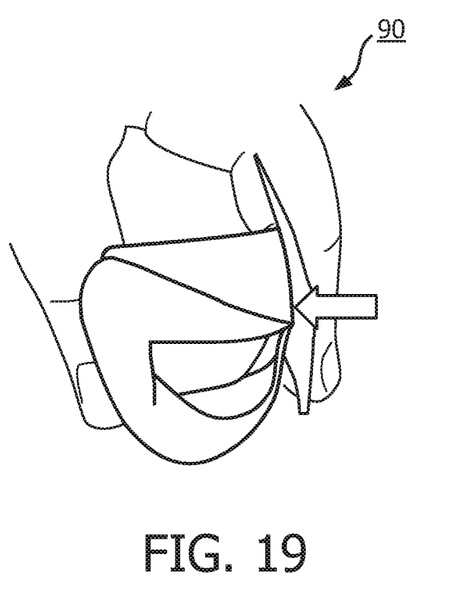
Figure 20:
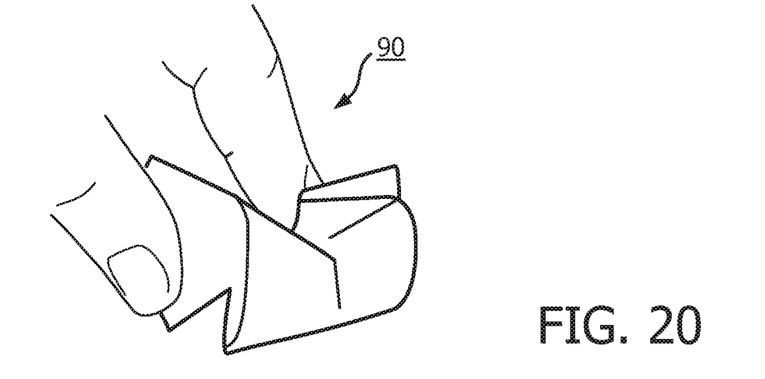
Figure 21:
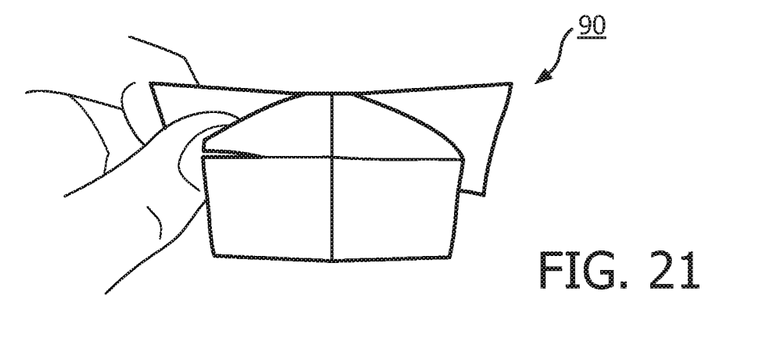

FIGS. 18 and 19 are side views of patient interface device 90, FIG. 20 is an isometric view of patient interface device 90, and FIG. 21 is a front view of patient interface device 90. Patient interface device 90 includes two offset parallel faceted conical surfaces. The inner surface contacts the base of the nose of a patient and the outer surface seals patient interface device 90, thus creating an air pillow. The air pillow inflates and pressure forces the inner surface to seal against the base of the nose. The facial contacting portion of patient interface device 90 includes a cup-like shape that captures the tip of the nose and resists hose torque.

Some examples of patient interface devices formed from foldable substrates have been described herein. However, it will be appreciated that various alterations may be made to substrates resulting in different patient interface device without departing from the scope of the disclosed concept. Any of the patient interface devices described herein, or other patient interface devices formed in accordance with the disclosed concept, may be employed with pressure support therapy systems such as system 2 described with respect to FIG. 1, or any other suitable type of pressure support therapy system. It will also be appreciated that patient interface devices formed in accordance with the disclosed concept may be employed in any other applications where nasal, nasal/oral, or full face masks are employed.

By providing foldable substrates that may be folded into patient interface devices, the cost of patient interface devices can be greatly reduced. For example, the foldable substrate may be formed from a low cost material such as paper backed by adhesive. Even if the patient interface device formed from the substrate is only used once or a few times, the substrate is so low cost that it can be a cost savings over a conventional reusable patient interface device. For example, a patient or healthcare provider may be sent a monthly supply of substrates that may be folded into patient interface devices as need, rather than providing the patient or healthcare provider with a conventional patient interface device.

It is contemplated that methods of forming patient interface devices from foldable substrates also fall within the scope of the disclosed concept. For example, in some embodiments, a method of forming a patient interface device includes providing a foldable substrate, such as substrate 10, or any substrate corresponding to any patient interface device described herein, folding said substrate along indicia provided on the substrate, and attaching adhesive sections of the substrate to other sections of the substrate to form the patient interface device.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An apparatus comprising:
    a patient interface device formed from a flat substrate that is folded, wherein the patient interface device includes a plurality of seams where sections of the substrate are joined together, and wherein one or more of the plurality of seams form a shape that corresponds to a perimeter of a bottom side of a nose from a first alare corner of the nose to a tip of the nose to a second alare corner of the nose;
    the patient interface device further includes a pair of openings in the substrate and a pair of accessory mounting adhesive sections, wherein each of the pair of accessory mounting adhesive sections surrounds a corresponding opening from the pair of openings; and
    at least one accessory item, wherein each of the at least one accessory item is structured to attach to a corresponding adhesive section from the pair of accessory mounting adhesive sections.

2. The apparatus of claim 1, wherein the plurality of seams includes a nasal interior perimeter seam that forms a shape that corresponds to a perimeter of a bottom side of a nose from a first alare corner of the nose to a tip of the nose to a second alare corner of the nose and a nasal exterior perimeter seam that forms a shape that corresponds to a perimeter of a bottom side of a nose from a first alare corner of the nose to a tip of the nose to a second alare corner of the nose.

3. The apparatus of claim 1, wherein the plurality of seams includes a centerline seam that extends along a centerline of the patient interface device.

4. The apparatus of claim 1, wherein the flat substrate includes one or more adhesive sections, and wherein the at least one of the plurality of seams is formed by joining sections of the substrate together with at least one of the adhesive sections.

5. An apparatus comprising:
    a substrate being structured to be foldable to form a patient interface device, wherein the patient interface device includes a plurality of seams where sections of the substrate are joined together, and wherein one or more of the plurality of seams form a shape that corresponds to a perimeter of a nose from a first alare corner of the nose to a tip of the nose to a second alare corner of the nose;
    the apparatus further comprising a pair of openings in the substrate and a pair of accessory mounting adhesive sections, wherein each of the pair of accessory mounting adhesive sections surrounds a corresponding opening from the pair of openings; and
    at least one accessory item, wherein each of the at least one accessory item is structured to attach to a corresponding adhesive section from the pair of accessory mounting adhesive sections.

6. The apparatus of claim 5, wherein the substrate includes a plurality of indicia indicating where to fold substrate to form the patient interface device.

7. The apparatus of claim 5, wherein the substrate includes a plurality of adhesive sections including adhesive and being structured to adhere to other sections of the substrate when the substrate is folded to form the patient interface device, and wherein at least one of the seams is formed by joining sections of the substrate together with at least one of the adhesive sections.

8. The apparatus of claim 7, wherein the substrate includes multiple layers including a top layer, a bottom layer, and an adhesive layer disposed between to the top and bottom layers.

9. The apparatus of claim 8, wherein the substrate includes a score line along an edge of one of the adhesive sections, wherein the score line is a cut through the top or bottom layer to the adhesive layer such that the top or bottom layer can be peeled off to expose the adhesive layer in the adhesive section.

10. The apparatus of claim 5, wherein the substrate includes a plurality of seam lines that correspond to the plurality of seams of the patient interface device, and wherein the plurality of seams includes a nasal interior perimeter seam that forms a shape that corresponds to a perimeter of a bottom side of a nose from a first alare corner of the nose to a tip of the nose to a second alare corner of the nose and a nasal exterior perimeter seam that forms a shape that corresponds to a perimeter of a bottom side of a nose from a first alare corner of the nose to a tip of the nose to a second alare corner of the nose.

11. The apparatus of claim 5, wherein the substrate includes a plurality of seam lines that correspond to the plurality of seams of the patient interface device, and wherein the plurality of seams includes a centerline seam that extends along a centerline of patient interface device.

12. The apparatus of claim 5, wherein the substrate includes at least one of paper, thin plastic, fabric, or lamination.

13. The apparatus of claim 5, wherein the substrate is structured such that the patient interface device has a V-shaped profile along a centerline of the patient interface device.

14. An apparatus comprising:
a first substrate being structured to be foldable to form a first part of a patient interface device, wherein the first part of the patient interface device is structured to cover a patient's nostrils and includes a plurality of seams where sections of the first substrate are joined together, and wherein one or more of the plurality of seams form a shape that corresponds to a perimeter of a bottom side of a nose from a first alare corner of the nose to a tip of the nose to a second alare corner of the nose; and a second substrate being structured to be foldable to form a second part of the patient interface device, wherein the second part of the patient interface device is structured to cover the patient's mouth, wherein the first part of the patient interface is structured to attach to the second part of the patient interface device to form the patient interface device;
the apparatus further comprising a pair of openings in the substrate and a pair of accessory mounting adhesive sections, wherein each of the pair of accessory mounting adhesive sections surrounds a corresponding opening from the pair of openings; and
at least one accessory item, wherein each of the at least one accessory item is structured to attach to a corresponding adhesive section from the pair of accessory mounting adhesive sections.

* * * * *